United States Patent
Herron

(10) Patent No.: US 10,070,998 B2
(45) Date of Patent: Sep. 11, 2018

(54) PREVENTION AND TREATMENT OF GROIN DERMATITIS METHODS AND SYSTEMS

(76) Inventor: Brandy K. Herron, Scottsbluff, NE (US)

(*) Notice: Subject to any disclaimer, the term of this patent is extended or adjusted under 35 U.S.C. 154(b) by 0 days.

(21) Appl. No.: 14/237,822

(22) PCT Filed: Aug. 9, 2012

(86) PCT No.: PCT/US2012/050111
§ 371 (c)(1),
(2), (4) Date: Feb. 7, 2014

(87) PCT Pub. No.: WO2013/023035
PCT Pub. Date: Feb. 14, 2013

(65) Prior Publication Data
US 2014/0188067 A1    Jul. 3, 2014

Related U.S. Application Data

(60) Provisional application No. 61/521,601, filed on Aug. 9, 2011.

(51) Int. Cl.
*A61F 13/49* (2006.01)
*A61F 13/505* (2006.01)
(Continued)

(52) U.S. Cl.
CPC ............ *A61F 13/513* (2013.01); *A61F 13/49* (2013.01); *A61F 13/49058* (2013.01);
(Continued)

(58) Field of Classification Search
CPC ........ A61F 13/51458; A61F 2013/4956; A61F 13/49003; A61F 13/49004;
(Continued)

(56) References Cited

U.S. PATENT DOCUMENTS 2,024,341 A * 12/1935 De Graff ............... A61F 5/4401
                                                              604/353
2,951,481 A *  9/1960 Gordon ................... A61F 13/68
                                                              2/400
(Continued)

FOREIGN PATENT DOCUMENTS

WO         2013023035         2/2013

OTHER PUBLICATIONS

PCT Application No. PCT/US2012/050111, Written Opinion dated Oct. 22, 2012.

(Continued)

*Primary Examiner* — Lynne Anderson
(74) *Attorney, Agent, or Firm* — Santangelo Law Offices, PC

(57) ABSTRACT

A unique garment designed to aid healing of minor skin ailments such as diaper rash. A urine absorbent, air flow permeable undergarment (1) may contain a barrier (4) to absorb urine and even an open back (5) such as for example a cutout in the back portion (3) a garment that may maximize airflow to the buttocks and groin. In some embodiments, a garment may not be a diaper and may not be designed to contain multiple urinations. In some embodiments, such as in a reusable form, the garment may be designed with a disposable pad capable of containing one or more urinations, then the disposable pad may be replaced. In yet another embodiment, a disposable garment may be provided so that after urination, the entire garment may be thrown away.

17 Claims, 6 Drawing Sheets

(51) Int. Cl.
*A61F 13/513* (2006.01)
*A61F 13/514* (2006.01)
*A61F 13/76* (2006.01)
*A61F 13/495* (2006.01)

(52) U.S. Cl.
CPC ...... *A61F 13/51458* (2013.01); *A61F 13/505* (2013.01); *A61F 13/76* (2013.01); *A61F 2013/4956* (2013.01); *A61F 2013/5055* (2013.01)

(58) Field of Classification Search
CPC .......... A61F 13/49006; A61F 13/49058; A61F 13/4915; A61F 13/493; A61F 13/505; A61F 13/66; A61F 13/68; A61F 13/70; A61F 13/74; A61F 13/76; A61F 13/80; A61F 2013/49068; A61F 2013/49082; A61F 2013/49098; A61F 2013/4953; A61F 2013/4955; A61F 2013/5055; A41B 13/04
USPC ...... 604/385.01, 385.11, 393, 394, 395, 396, 604/392; 2/111
See application file for complete search history.

(56) References Cited

U.S. PATENT DOCUMENTS

| | | | |
|---|---|---|---|
| 3,616,798 A * | 11/1971 | Garfinkel | A61F 13/64 604/370 |
| 3,964,486 A | 6/1976 | Blaney | |
| 4,235,237 A | 11/1980 | Mesek et al. | |
| 4,657,537 A | 4/1987 | Zimmerer | |
| 4,673,402 A | 6/1987 | Weisman et al. | |
| 4,685,909 A | 8/1987 | Berg et al. | |
| 4,842,593 A | 6/1989 | Jordan et al. | |
| 4,887,602 A | 12/1989 | O'Leary | |
| 4,930,161 A * | 6/1990 | Cohen | A41D 13/1254 2/114 |
| 5,069,672 A * | 12/1991 | Wippler | A61F 13/62 604/385.14 |
| 5,137,525 A | 8/1992 | Glassman | |
| 5,207,663 A * | 5/1993 | McQueen | A61F 5/4401 2/400 |
| 5,239,706 A * | 8/1993 | Stevenson | A41D 1/06 2/400 |
| 5,695,488 A * | 12/1997 | Sosalla | A61F 13/49011 604/385.24 |
| 5,876,395 A * | 3/1999 | Hart | A61F 13/66 2/401 |
| 6,102,899 A * | 8/2000 | Yimin | 604/385.01 |
| 6,393,621 B1 | 5/2002 | Redwine et al. | |
| 6,616,649 B1 | 9/2003 | Ismail | |
| 6,627,178 B1 | 9/2003 | Cawthon | |
| 6,803,045 B1 | 10/2004 | Goldberg | |
| 6,863,666 B2 | 3/2005 | Minato | |
| 7,137,972 B1 * | 11/2006 | Holberg | A61F 13/4915 604/347 |
| 7,850,671 B1 | 12/2010 | Burrows | |
| 2003/0114828 A1 | 6/2003 | Minato | |
| 2003/0149418 A1 | 8/2003 | Katz | |
| 2004/0167483 A1 | 8/2004 | Gabbay | |
| 2004/0167485 A1 | 8/2004 | Gabbay | |
| 2004/0210206 A1 | 10/2004 | Coates | |
| 2005/0090795 A1 | 4/2005 | Coleman | |
| 2005/0203476 A1 | 9/2005 | Stegall | |
| 2007/0083171 A1 | 4/2007 | Lynn | |
| 2008/0119813 A1 | 5/2008 | Carstens | |
| 2009/0036852 A1 * | 2/2009 | Suzuki et al. | 604/367 |
| 2010/0022979 A1 | 1/2010 | Carnegie et al. | |
| 2010/0191208 A1 * | 7/2010 | Kane | 604/385.01 |
| 2011/0028926 A1 | 2/2011 | Davis | |
| 2011/0092942 A1 | 4/2011 | Ruman et al. | |

OTHER PUBLICATIONS

PCT Application No. PCT/US2012/050111, Search Report dated Oct. 22, 2012.
U.S. Appl. No. 61/521,601, filed Aug. 9, 2011, entitled "Methods and Systems for Prevention and Treatment of Groin Dermatitis".

* cited by examiner

PREVENTION AND TREATMENT OF GROIN DERMATITIS METHODS AND SYSTEMS

PRIORITY CLAIM

This application is the U.S. National Stage of International Application No. PCT/US2012/050111, filed Aug. 9, 2012, which claims the benefit of and priority to U.S. Provisional Application No. 61/521,601 filed Aug. 9, 2011, each application hereby incorporated by reference herein in its entirety.

TECHNICAL FIELD

Generally, this invention relates to a garment for use in a manner as to facilitate healing of skin irritations in the general area of the groin and buttocks. Specifically, the invention focuses on garment systems which may allow air circulation to perhaps keep the area around the groin and buttocks dry while even minimizing contact with fabric.

BACKGROUND OF THE INVENTION

The desire to maintain airflow in the groin and buttocks region while absorbing urine and perhaps other waste has been a continuous dilemma in the personal hygiene industry. Perhaps one of the most significant problems that those in the personal hygiene industry have faced may be how to absorb urine while allowing airflow. When skin in the groin and buttocks is continuously exposed to wetness without adequate air exposure, skin irritations such as diaper rash may ensue.

Another problem that may occur is how to facilitate healing diaper rash or other skin irritations that may require exposure to air while absorbing urine perhaps without using ointments, creams, pastes, or the like. Physicians may recommend exposing the groin and buttocks to air to speed healing of such skin irritations. While removing an undergarment, such as cloth or disposable diapers, from a child or person may maximize airflow to the groin and buttocks, there is nothing left to absorb urine.

The present invention solves the above mentioned problems. The invention can absorb urine while allowing the groin and buttocks to be exposed to air. Thus facilitating the healing of skin irritations such as, but not limited to, diaper rash while protecting items such as furniture and flooring from exposure to urine by persons lacking bladder control.

A key application of the present invention may be in the personal hygiene industry. A significant aspect of the personal hygiene industry may include the use of items made to absorb urine such as cloth and disposable diapers. Prior to the present invention, past impediments to maximizing airflow may be the incorporation of a solid, non-permeable cover over the buttocks and groin and perhaps even the materials used in the manufacturing process that are designed to hold in wetness.

As to the personal hygiene industry and the overall desire to absorb urine and maximize airflow, the present invention discloses techniques which overcome virtually every one of the previous problems in a practical fashion.

Attempts have been made in the past to solve the problems that those in the personal hygiene industry have faced in attempting to practically absorb urine and maximize airflow. In spite of those attempts, until the present invention, no techniques were available which practically solved the above mentioned problems.

DISCLOSURE OF THE INVENTION

The present invention includes a variety of aspects which may be selected in different combinations based upon the particular application or needs to be addressed. In one basic form, the invention may utilize a garment with an absorbent pad that may fasten around the waist or may be a pull-up type garment either with a cutout in the material over the buttocks perhaps allowing complete exposure of the skin to air. The present invention has been found to absorb urine while maximizing the flow of air to the buttocks and facilitating healing of diaper rash. A benefit of this garment may be that a person who lacks bladder control, such as a child, is able to benefit from direct airflow to the affected region while protecting flooring and furniture from urine. A feature of the design may be that it does not trap wetness in the buttock and groin region. In some embodiments, while the garment may be constructed of sturdy, reusable fabric that can be cleaned and sanitized in the washing machine and dryer, the removable absorbent pad may be intended for one use. The present invention may also include a customizable fit.

In another form, the invention may utilize a garment design with a cutout in the material over the buttocks, but the absorbent pad may be built into the garment. In this form, the garment may be made of disposable materials and may be intended for one time use.

Another example of an embodiment of the present invention may provide a garment design which can be constructed of reusable or even disposable materials perhaps with a corresponding removable or even built-in absorbent pad. In some embodiments, a material cutout over the buttocks may be covered allowing maximum airflow while providing modest coverage of the buttocks.

A broad objective of the present invention may be to provide an aid to healing skin ailments such as diaper rash. Thus, one goal may include providing a garment that may absorb urine while allowing for airflow in the critical areas such as the groin and buttocks. While urine absorbing garments may already exist, a goal of the present invention is to achieve urine absorbency while adding the element of maximized airflow to the regions prone to skin irritation such as diaper rash. This may be achieved through the cutout in the buttock region of the garment as discussed herein.

Naturally, further objects, goals and embodiments of the inventions are disclosed throughout other areas of the specification and claims.

MODE(S) FOR CARRYING OUT THE INVENTION

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The present invention may involve providing a garment that may absorb urine perhaps through an absorbent pad while allowing maximum airflow to the buttocks and groin perhaps through the use of a cutout in a back of the garment.

Embodiments of the present invention may provide a urine absorbent, air flow permeable undergarment comprising a front portion of said urine absorbent, air flow permeable undergarment, a non-absorbent air circulating back portion of said urine absorbent, air flow permeable undergarment; and perhaps even a urine absorbing barrier in said front portion of said urine absorbent, air flow permeable undergarment. Methods may include providing air circulation in undergarment articles comprising the steps of providing a urine absorbing, air flow permeating undergarment; collecting urine in a front portion of said urine absorbing, air flow permeating undergarment; and perhaps even circulating air to a non-absorbent back portion of said urine absorbing, air flow permeating undergarment.

Figure 1:
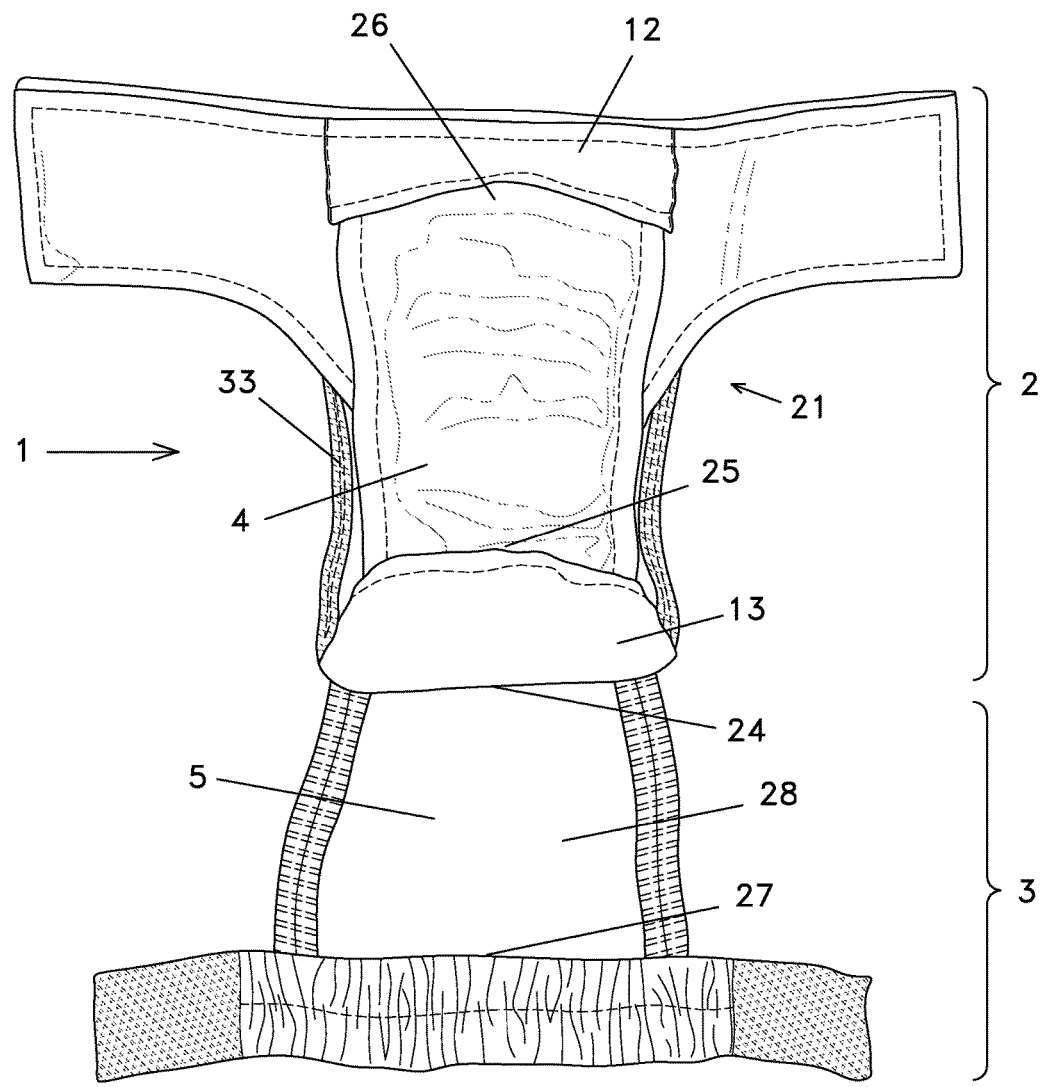
FIG. 1 shows an example of a garment in accordance with embodiments of the present invention.
Figure 2:
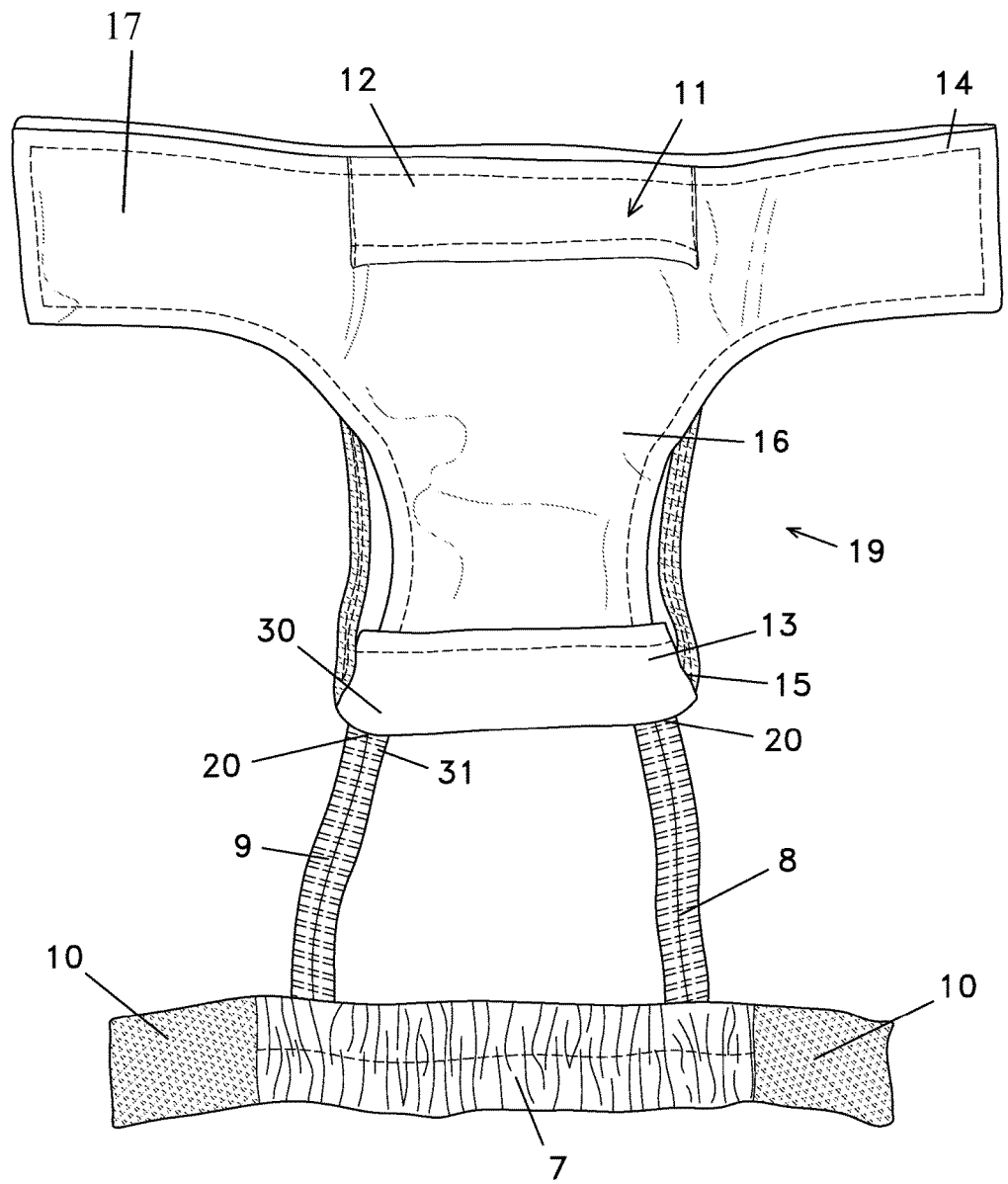
FIG. 2 shows an example of a garment as in FIG. 1 without an absorbent barrier such as a pad in accordance with embodiments of the present invention.

As may be understood from FIGS. 1 and 2, a urine absorbent, air-flow permeable undergarment (1) may include a front portion (2), a back portion (3) such as a non-absorbent air circulating back portion, and perhaps even a urine absorbing barrier (4) in a front portion (2). This may provide an undergarment that can circulate air to a back portion of a garment while collecting urine in a front portion to perhaps allow prevention, healing, or even treatment of groin dermatitis, diaper rash, or the like perhaps even while retaining urine. Each portion of a garment may be any part of a whole perhaps separated from or even integrated with or the like.

Figure 4:
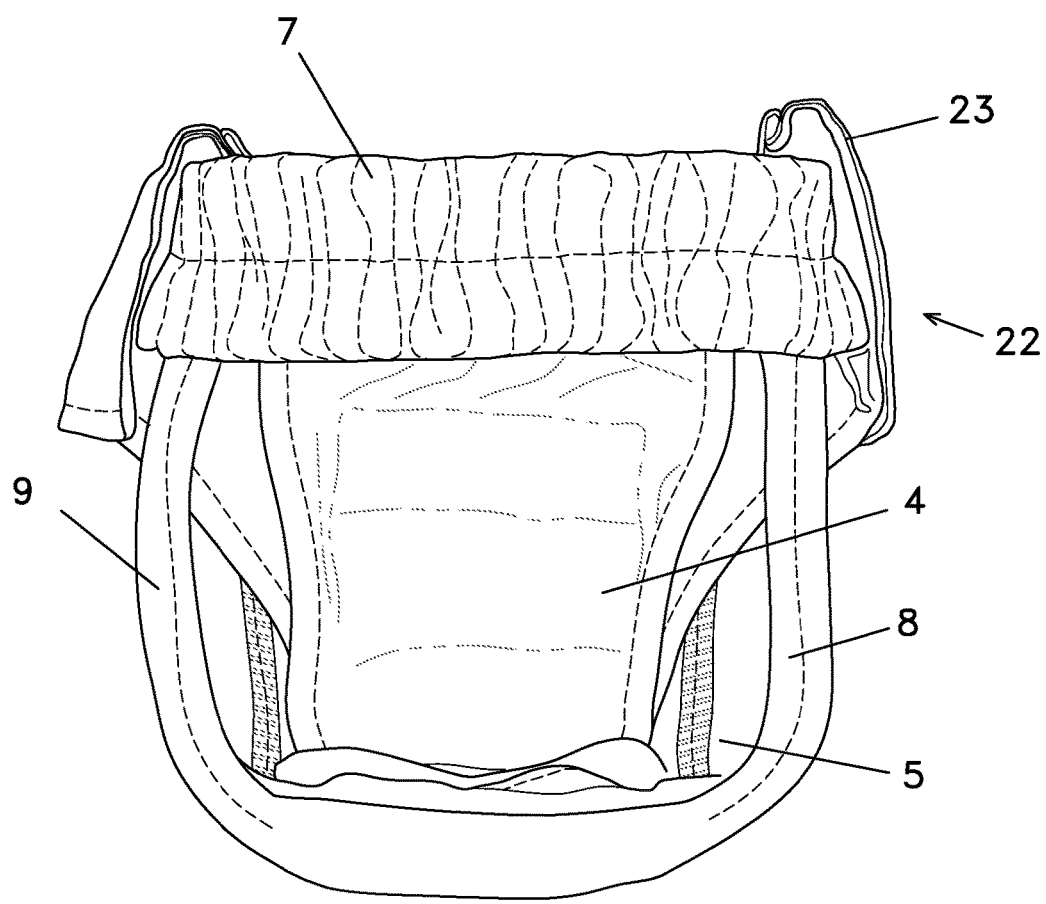
FIG. 4 depicts a rear view of an embodiment of the present invention showing an open cutout.

A back portion (3) of an undergarment may be non-absorbent and may provide air circulation to the user's buttocks and perhaps even part of a groin area. In some embodiments, this may be provided by use of an air permeable material on a back portion, a porous material on a back portion, by providing an open back (5) or the like in a back of a garment. An open back (5) which may be an opening, cutout, hole or the like or even more than one opening, cutout, holes or the like in a back of a garment, may provide an opening over a buttocks area (28) and a groin area (24). In a back portion of a garment, a groin area may begin just above the bottom curve of the buttocks. This may expose the buttocks and at least some of a groin area to air and may even provide substantial exposure of at least some skin to air for the treatment or even prevention of skin ailments. This may be understood by the design shown in FIG. 1 and how a garment may be situated when in use as understood from FIG. 4 which shows a back view of the garment. An open back (5) may be a cutout having a any shape which may include but is not limited to a trapezoid, an inverted trapezoid, circle, oval, rectangle, square, round, triangle, any combination thereof, or the like. An open back (5) may be a cutout that may be placed or located below a waistband (27) to a groin area (24) which may allow for maximum airflow. As one example, a cutout may take the shape of an inverted trapezoid with the left and right sides comprised of straps that may hug the child's buttocks perhaps with an elasticized fit. The top and bottom edges of the trapezoid may also contain elastic. The bottom edge of the cutout may contain a small pocket to conceal the edge of the pad.

Figure 6:
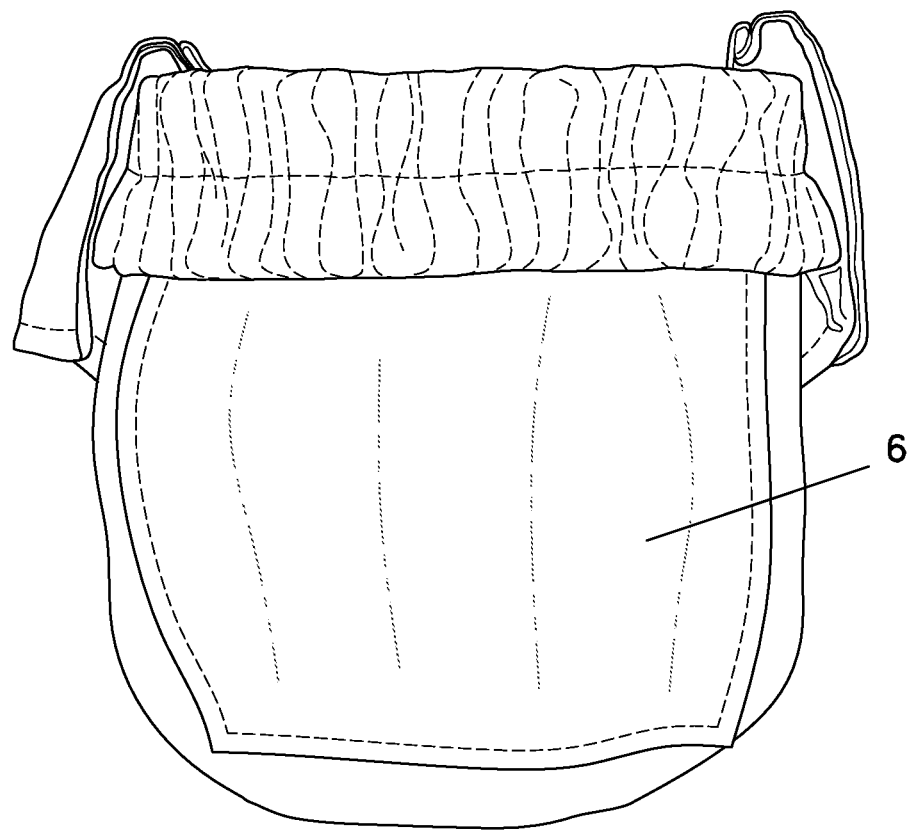
FIG. 6 depicts an alternative embodiment of the present invention showing a rear view with a cover over a cutout.

Of course, any kind of open back may be used including any kind of shape, size, material, or the like and may be completely open, partially open, covered with a cover, or the like. A back portion may be covered with a cover (6) perhaps to cover a cutout while allowing air circulation. A cover may be anything that may extend or even partially extend over a back portion and may include, but is not limited to, a cape, a mesh cover, a gauze cover, gauze type fabric a tutu, a skirt, a flap, shorts, pants, dress, clothing, porous material, air permeable material, any combination thereof, or the like or as understood in the non-limiting example shown in FIG. 6.

In some embodiments, a permanently non-absorbent back portion may be used where perhaps, at all times, the garment may not have an absorbent back portion. For example, in some embodiments, a garment may not have an absorbent back portion at all. To further explain, in some embodiments, a garment may have a non-tearable back portion in that a user may not be able to tear out part or even any of a back portion to allow air flow or remove absorbent materials or the like. Of course, in other embodiments, a garment may have an absorbent or even tearable back portion.

A back portion (3) of a garment may be a non-containment back portion or even a non-solid waste containment back portion such that a back portion may not contain any solid waste or the like. A back portion of a garment may have a waist band (7) and perhaps even two side bands (8), (9), a non-limiting example thereof is shown in FIG. 2. The use of a waist band and two side bands in the back portion of a garment may provide an open back as discussed herein. A waist band (7) (e.g., a back waist band or a front waist band) and two side bands (8), (9) may be a strip of material, may be a thin flat strip of material, may be a strap, may be flexible, may be adjustable, or the like. The two side bands (8), (9) may be configured to hug the sides of a user's buttocks perhaps to provide hugging of the back portion of the garment to the user. This may allow securement to the user and may even allow air circulation as discussed herein. An adjustable band may provide adjustment of a band (e.g., a waist band, a front waist band, a back waist band, side bands, or the like) perhaps to allow ease of putting on or taking off the garment, adjustability to provide a customized fit the user and adapt to different user's sizes and shapes, or the like. An adjustable band may include, but is not limited to, a flexible band, a band with adjustable snaps, a band with adjustable buttons, an elastic band, an inflexible band with adjustments, an adjustment between a front and back waist band, any combination thereof, or the like.

In embodiments, the present invention may provide fastening a front portion to a back portion of a garment with a fastener. For example, a garment may fasten around the child's waist perhaps by locating a fastener on a waist band. A fastener (10) may be on a back portion of a garment which can fasten to fastener (18) on a front portion of a garment. As shown in FIG. 2, a fastener (10) is located at each end of a waist band and may be wrapped around a user and fastened to a fastener (18) which may be located at each end of a front portion of a garment. Of course, a fastener may be placed at any location of the garment including but not limited to at the top, middle, bottom, sides, ends, horizontally, vertically, diagonally or the like and may even provide one fastener, two fasteners, or more or the like. A fastener may include, but is not limited to, a hook and loop fastener, snaps, buttons, button closures, Velcro, zippers, ties, laces, cord, bungee cord, adhesive, reusable fasteners, any combination thereof, or the like. A fastener may allow for size adjustment and ease of use. Alternative closers and fasteners may be used and it is anticipated that any type of fastener may be used in the garment.

A urine absorbing barrier (4) in a front portion of a garment may provide containment of urine in a garment. In some embodiments, a urine absorbing barrier (4) may be a pad or even an absorbent pad or other type of absorbent element, as show in the non-limiting example in FIG. 1 and FIG. 4. The absorbent pad may have a proper absorption level to contain the amount of urine specific to the age of the wearer of the garment. A pad may be manufactured in a customized size specific to the garment or the pad may even have modifications available to absorb urine more effectively based on gender. Attaching an absorbent pad could be provided by an adhesive strip or other fasteners or may even be attached with a pocket sewn into the groin of the garment as discussed herein.

A urine absorbing barrier such as a pad may be attached to a garment, may be removably attached to a garment, may be permanently attached to a garment, may be incorporated perhaps to make part of a garment, or the like. Thus, in some embodiments a urine absorbing barrier (4) may be a pad that can be attached and even removed from a garment. A urine absorbing barrier such as a pad may be disposable so that a pad, for example, can be thrown out or perhaps even a urine absorbing barrier may be reusable so that a pad, for example, that can be washed, reused, or even removed, washed and reused. Attachment of a urine absorbing barrier may be any kind of securement of a barrier to a garment. A urine absorbing barrier (4) may be placed or even located lengthwise from a groin area (25) of a front portion extending forward to a top (26) of a front portion of an undergarment as may be understood in the non-limiting example in FIG. 1. Further, in embodiments, a garment may have an absorbent pad placed at the length of the groin from the crotch area extending forward to the top of the garment. Of course, any location for a urine absorbing barrier may be used and all are meant to be included in this disclosure.

As mentioned, embodiments of the present invention may provide a fastener for a urine absorbing barrier. A fastener may be used to attach, permanently attach, removably attach, or the like a urine absorbing barrier to a garment, for example to an inside of a front portion. A fastener may include, but is not limited to, a pad attachment (11), a pad holder, a pocket, an adhesive, an adhesive strip, snaps, or the like fasteners. Alternatively, in embodiments, the present invention may provide an air circulating undergarment that does not have any urine absorbing barriers.

As discussed herein, an undergarment may have a front portion (2) which may include a urine absorbing barrier attachment, such as a pad attachment (11) so as to provide attachment of a urine absorbing barrier, e.g., a pad, to a garment. A pad attachment (11) may be a pad holder, a pocket, a pocket enclosure, to end pockets, fasteners, or the like. As shown in the non-limiting example in FIG. 1, end pockets (12) and (13) may be provided in the garment so that ends of a pad can be inserted, placed, concealed, or can even be held in the garment. The end pockets may be located at or near a top (14) of an inside of a front portion (where end pocket (12) is shown in FIG. 1 and FIG. 2) and perhaps even at a bottom (15) of an inside of a front portion (where end pocket (13) is shown in FIG. 1 and FIG. 2). End pockets may be small pockets perhaps to conceal or even hold an edge of a pad. FIG. 2 shows non-limiting examples of end pockets with the pad removed from the garment. Of course a pocket, end pockets or any other kind of pad attachment may be located or utilized in any part of the garment such as at the sides, as a fully enclosed pocket or pad so that the pad may fully enclose the perimeter of a pad, or the like.

A front portion (2) of an undergarment may include a front groin panel (16) and may even include a front waist band (17) as understood from the non-limiting example in FIG. 1. A front portion (2) of an undergarment may be made of any kind of material including but not limited to a breathable material, a single layer of material, multi-layered materials, disposable materials, recyclable materials, or the like. A front portion (2) may have two side thigh bands (33), as shown in the non-limiting examples in FIGS. 1 and 3 and may be elastic or the like perhaps providing hugging to a user's inner thighs. The side thigh bands may fit around a thigh and may provide a snug fit against a body. This may assist in preventing leakage of urine or help secure the garment to the user or the like.

In embodiments, an undergarment may be a one-piece undergarment (19) so that the materials are one piece. It is noted that a one-piece undergarment may use a removable pad or may even have a urine absorbing barrier incorporated therein. A one-piece garment may be configured like a diaper, cloth diaper, or the like in that it may be attached and unattached (e.g., opened) at a waist band when securing and removing the garment to a user. Securement and/or removal of a garment may be achieved when a user may be laying down, standing up, or even sitting, or the like. For example, a front portion of a waist band may be attached or even removably attached (perhaps in a use position) (22) and may be unattached (perhaps in a non-use position) (21) from a back portion of a garment. In some embodiments, a pattern may be cut so a layer or even each layer may be one piece perhaps with an adjustable elastic waistband. Alternatively, a one-piece garment may be permanently attached at a waist line such as by a waist band, perhaps as understood in FIG. 3, where in order to put on and take off the garment, a user can pull up or pull off the garment over their feet and legs such as in a pull up style one piece undergarment. In alternative embodiments, the garment may be more than one piece, perhaps that a front portion (2) may be separate from a back portion (3) thus providing a separate front and separate back portion or the like. In this fashion, the front portion and back portion may then be attached before use or when putting securing to a user. A bottom of a front portion (30) may be attached (20) to the bottom of a back portion (31) to perhaps provide bottom attachment of the two pieces. For example, each end of the side bands may be attached to the bottom of a front portion. Attachment may be by any kind of attachment as discussed herein and as may be understood in the art.

Figure 3:
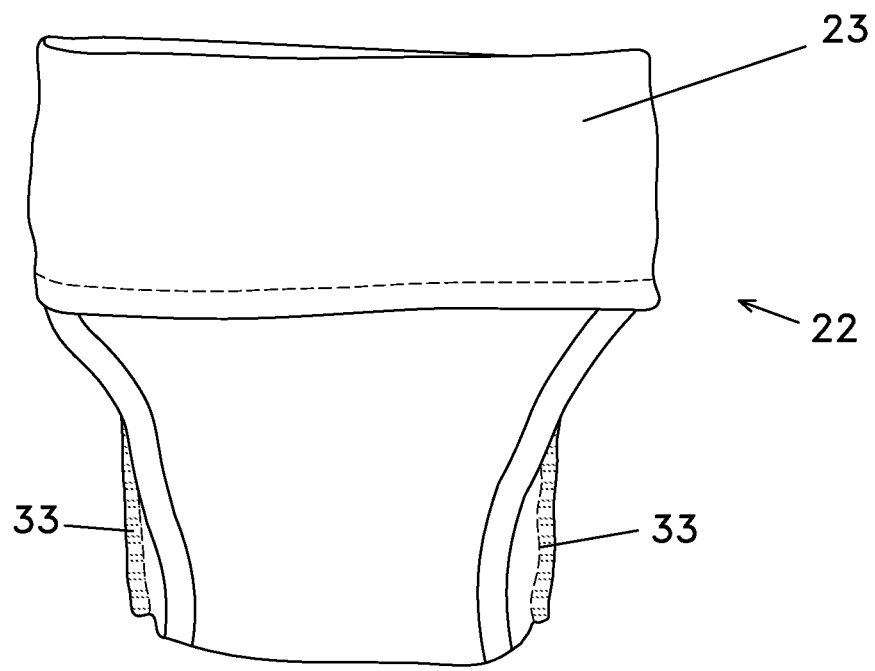
FIG. 3 depicts a frontal view of an embodiment of the present invention.
Figure 5:
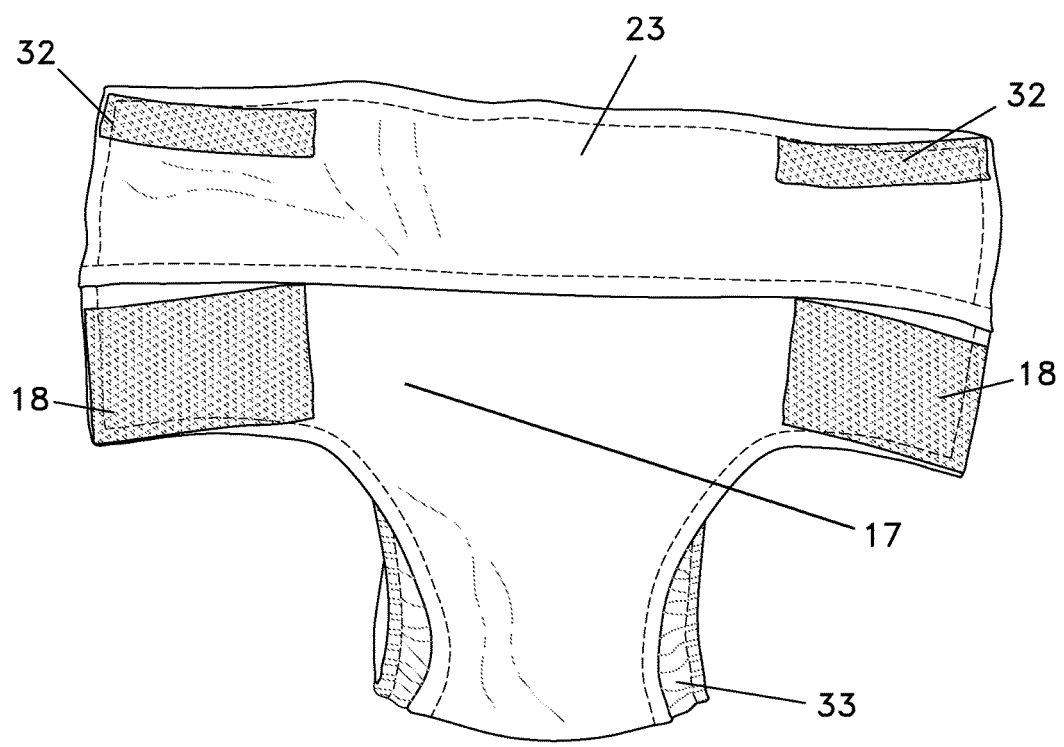
FIG. 5 shows an example of a front view of a garment with a front cover flap in accordance with embodiments of the present invention.

In embodiments, the present invention may provide covering at least part of a front portion of a garment with perhaps a front cover flap (23) as may be understood in the non-limiting examples shown in FIG. 3 and FIG. 5. A front cover flap may be used to prevent a user (such as a child) from detaching a front portion from a back portion, may be used as an aesthetic element, or the like. A front cover flap may be an extended flap of material on the top of a front portion of a garment that may fold over and may even fasten with a front cover flap fastener (32) to the front of the front portion of a garment. As shown in FIG. 5, two fasteners (32)

are used to attach a cover flap to a fastener (18) on a front portion. In embodiments, a fastener (18) may have a dual purpose perhaps to provide fastening of a back portion to the front portion and to provide fastening of a cover flap to a front portion. When putting on a garment in this fashion, a user may attach the back portion to a front portion perhaps at the waist band and then may fold a cover flap over the front and attach the front cover flap to the front portion of the garment.

As mentioned, embodiments of the present invention may provide a garment that may be constructed of disposable or perhaps even reusable materials. A garment may be constructed with one, two, or more layers of materials such as breathable fabric or the like. A garment may be sewn together in a manner that may require no closure perhaps similar to underwear. A garment may be fully disposable, partially disposable, reusable, or even partially reusable. As could be easily appreciated, there are a variety of ways to construct a garment. One example may be to utilize traditional thread to sew the layers of fabric together. An alternative may be to use elastic thread. Another option may be to use a no-sew heat activated adhesive. Each alternative could be used in a reusable or disposable garment.

Alternative examples of a garment may include but, are not limited to, an interior pouch for a pad, a modified pattern cut, elasticized straps, button or even snap closures, an adjustable waist which may be located on the inside, any combination thereof, or the like. In embodiments, a urine absorbing barrier may be permanently attached to a garment so that the garment may be completely reusable, perhaps when urine is absorbed, the entire garment may be washed and reused with the barrier attached therein. Alternatively, a barrier may be removed perhaps to be washed or even disposed and the garment may be washed and reused. In yet another alternative embodiment, a garment may be disposed completely after use.

As can be easily understood from the foregoing, the basic concepts of the present invention may be embodied in a variety of ways. It involves both air flow providing garment techniques as well as devices to accomplish the appropriate garment. In this application, the garment techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "fastener" should be understood to encompass disclosure of the act of "fastening"—whether explicitly discussed or not—and, conversely, were there effectively disclosure of the act of "fastening", such a disclosure should be understood to encompass disclosure of a "fastener" and even a "means for fastening." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of references below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

| U.S. PATENTS | | |
| --- | --- | --- |
| Pat. No. | Issue Date | Name of Patentee or Applicant of cited Document |
| 7,850,671 | 2010 Dec. 14 | Burrows |
| 6,803,045 | 2004 Oct. 12 | Goldberg |
| 6,627,178 | 2003 Sep. 30 | Cawthon |
| 5,137,525 | 1992 Aug. 11 | Glassman |
| 4,887,602 | 2989 Dec. 29 | O'Leary |
| 4,842,593 | 1989 Jun. 27 | Jordan et al. |
| 4,685,909 | 1987 Aug. 11 | Bergetal. |
| 4,673,402 | 1987 Jun. 16 | Weisman et al. |
| 4,657,537 | 1987 Apr. 14 | Zimmerer |
| 3,964,486 | 1976 Jun. 22 | Blaney |
| 6,863,666 | 2005 Mar. 8 | Minato |
| 4,235,237 | 1980 Nov. 25 | Mesek et al. |

| U.S. PATENT APPLICATION PUBLICATIONS | | |
| --- | --- | --- |
| Publication Number | Publication Date | Name of Patentee or Applicant of cited Document |
| 20110028926 | 2011 Feb. 3 | Davis |
| 20070083171 | 2007 Apr. 12 | Lynn |
| 20050203476 | 2005 Sep. 15 | Stegall |
| 20040167485 | 2004 Aug. 26 | Gabbay |
| 20040167483 | 2004 Aug. 26 | Gabbay |
| 20030114828 | 2003 Jun. 19 | Minato |
| 20030149418 | 2003 Aug. 7 | Katz |

| NON-PATENT LITERATURE DOCUMENTS Name of Document |
| --- |
| Provisional application number 61/521,601; filed Aug. 9, 2011; entitled Methods and Systems for Prevention and Treatment of Groin Dermatitis |

Thus, the applicant(s) should be understood to have support to claim and make a statement of invention to at least: i) each of the garment devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC*, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A garment comprising:
   a front portion of an urine absorbent, air flow permeable undergarment;
   wherein said front portion of said urine absorbent, air flow permeable undergarment, includes a front groin panel and a front waist band, wherein said front waist band outwardly extends from said front groin panel and is configured to cover a front side of each of a user's hips;
   a non-absorbent air circulating back portion of said urine absorbent, air flow permeable undergarment;
   wherein said non-absorbent air circulating back portion of said urine absorbent, air flow permeable undergarment does not have a urine absorbing barrier;
   wherein said non-absorbent air circulating back portion of said urine absorbent, air flow permeable undergarment comprises a waist band, two side bands, each of which are configured to hug each side of a user's buttocks, and an open back cutout defined by said waist band and said two side bands and which said open back cutout creates complete bare exposure of substantially all of a user's buttocks and intergluteal cleft when worn;
   wherein said non-absorbent air circulating back portion is configured to provide substantial air exposure to a user's buttocks, user's intergluteal cleft, and part of a user's groin;
   wherein said two side bands are each fixedly attached to an opposite end of a linear bottom part of said front portion of said urine absorbent, air flow permeable undergarment allowing the middle of said linear bottom part of said front portion to be free from straps;
   a urine absorbing barrier in said front portion of said urine absorbent, air flow permeable undergarment;
   a back band fastener located on a back waist band of said non-absorbent air circulating back portion, wherein said back band fastener is configured to fasten to a front band fastener located on said front waist band of said front portion of said urine absorbent, air flow permeable undergarment, wherein said front waist band is separate from said back waist band; and
   a front cover flap on said front portion of said urine absorbent, air flow permeable undergarment configured to fold over substantially all of said front waist band of said front portion and is configured to fold over at least part of each end of said back waist band of said back portion of said urine absorbent, air flow permeable undergarment when said back waist band is attached to said front waist band.

2. A garment according to claim 1 wherein said non-absorbent air circulating back portion of said urine absorbent, air flow permeable undergarment comprises a non-tearable back portion of said urine absorbent, air flow permeable undergarment.

3. A garment according to claim 1 wherein said cutout comprises a shape selected from a group consisting of a trapezoid, an inverted trapezoid, circle, oval, rectangle, square, round, triangle, and any combination thereof.

4. A garment according to claim 1 wherein said front portion of said urine absorbent, air flow permeable undergarment comprises a pad attachment.

5. A garment according to claim 4 wherein said pad attachment comprises two end pockets.

6. A garment according to claim 5 wherein said end pockets are located at a top and a bottom of an inside of said front portion.

7. A garment according to claim 1 wherein said urine absorbing barrier comprises an absorbent pad.

8. A garment according to claim 1 wherein said urine absorbing barrier is configured to be placed lengthwise from a groin area of said front portion extending forward to a top of said front portion of said urine absorbent, air flow permeable undergarment.

9. A garment according to claim 1 wherein said back band fastener and said front band fastener are selected from a group consisting of a hook and loop fastener, snaps, buttons, button closures, zippers, ties, laces, cord, bungee cord, adhesive, reusable fasteners, and any combination thereof.

10. A garment according to claim 1 and further comprising a front cover flap fastener.

11. A method of providing air circulation in undergarment articles comprising the steps of:
   providing a urine absorbing, air flow permeating undergarment comprising a front portion and a back portion, wherein said front portion of said urine absorbing, air flow permeating undergarment comprises a front groin panel and a front waist band, wherein said front waist band outwardly extends from said front groin panel and is configured to cover a front side of each of a user's hips;
   fastening said back waist band of said back portion to said front waist band of said front portion of said urine absorbing, air permeating undergarment with a back band fastener located on said back waist band of said back portion and a front band fastener located on said front waist band of said front portion, wherein said front waist band is separate from said back waist band;
   providing a front cover flap on said front portion;
   folding said front cover flap over substantially all of said front waist band of said front portion and over at least part of each end of said back waist band of said non-absorbent air circulating back portion of said urine absorbent, air flow permeable undergarment when said back waist band is attached to said front waist band;

collecting urine in an urine absorbing barrier in said front portion of said urine absorbing, air flow permeating undergarment;

exposing substantially all of a user's buttocks and intergluteal cleft with an open back cutout defined by a waist band and two side bands of said back portion when wearing said urine absorbing, air flow permeating undergarment, wherein said open back cutout creates complete bare exposure of substantially all of a user's buttocks and intergluteal cleft when worn; wherein said two side bands are each fixedly attached to an opposite end of a linear bottom part of said front portion of said urine absorbent, air flow permeable undergarment allowing the middle of said linear bottom part of said front portion to be free from straps;

circulating air to a substantial portion of a user's buttocks, said user's intergluteal cleft, and part of said user's groin when wearing said non-absorbent back portion of said urine absorbing, air flow permeating undergarment; and treating said user's diaper rash with said urine absorbing, air flow permeating undergarment.

12. A method of providing air circulation in undergarment articles according to claim 11 wherein said step of circulating air to a substantial portion of a user's buttocks, said user's intergluteal cleft, and part of said user's groin when wearing said non-absorbent back portion of said urine absorbing, air flow permeating undergarment comprises the step of continuously circulating air to a substantial portion of a user's buttocks and part of said user's groin when wearing said non-absorbent back portion of said urine absorbing, air flow permeating undergarment.

13. A method of providing air circulation in undergarment articles according to claim 11 and further comprising the step of hugging each side of buttocks with said side bands.

14. A method of providing air circulation in undergarment articles according to claim 11 wherein said step of collecting urine in a front portion of said urine absorbing, air flow permeating undergarment comprises the steps of:

absorbing said urine with a pad; and placing two ends of said pad into a two end pockets of said front portion of said urine absorbing, air flow permeating undergarment.

15. A method of providing air circulation in undergarment articles according to claim 14 and further comprising the step of locating said end pockets at a top and a bottom of said front portion of said urine absorbing, air flow permeating undergarment.

16. A method of providing air circulation in undergarment articles according to claim 11 and further comprising the step of reusing said urine absorbing, air flow permeating undergarment.

17. A method of providing air circulation in undergarment articles according to claim 11 wherein said back band fastener and said front band fastener are selected from a group consisting of a hook and loop fastener, snaps, buttons, button closures, zippers, ties, laces, cord, bungee cord, adhesive, reusable fasteners, and any combination thereof.

* * * * *